US00PP24291P3

(12) United States Plant Patent
Egger

(10) Patent No.: US PP24,291 P3
(45) Date of Patent: Mar. 4, 2014

(54) ***HEUCHERA* PLANT NAMED 'BELLA NOTTE'**

(50) Latin Name: ***Heuchera* sp.**
Varietal Denomination: Bella Notte

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 148 days.

(21) Appl. No.: 13/506,804

(22) Filed: May 16, 2012

(65) Prior Publication Data

US 2013/0312147 P1 Nov. 21, 2013

(51) Int. Cl.
*A01H 5/00* (2006.01)

(52) U.S. Cl.
USPC ..... Plt./440

(58) Field of Classification Search
USPC ..... Plt./440
See application file for complete search history.

*Primary Examiner* — June Hwu
(74) *Attorney, Agent, or Firm* — Klarquist Sparkman, LLP

(57) ABSTRACT

A new and distinct *Heuchera* plant characterized by medium large, near black leaves with a slight white veil year round, short, dark peduncles, large, bicolor dark and light pink flowers that continue to bloom spring, summer and fall, a well branched, medium large, mounding habit, and excellent vigor.

1 Drawing Sheet

Botanical denomination: *Heuchera* sp.
Variety designation: 'Bella Notte'.

BACKGROUND OF THE INVENTION

The present invention relates to a new and distinct cultivar of *Heuchera* and given the cultivar name of 'Bella Notte'. *Heuchera* is in the family Saxifragaceae. *Heuchera* 'Bella Notte' originated from a planned cross for a black leaf, attractive flowering *Heuchera.* This cross was between *Heuchera* K355-3, a proprietary non-commercial hybrid, as the seed parent, and *Heuchera* K367-2, a proprietary non-commercial hybrid, as, as the pollen parent.

Compared to the seed parent, *Heuchera* K355-3, the new cultivar is similar, but with a much better crown count and the leaves of the new cultivar are larger and have only a very light veil rather than veiled.

Compared to the pollen parent, *Heuchera* K367-2, the new cultivar has larger leaves and warm pink flowers rather than yellow to red flowers.

Compared to *Heuchera* 'Swirling Fantasy', U.S. Plant Pat. No. 14,542, the new cultivar has much blacker leaves with shorter flowering stems of larger, darker pink flowers.

Compared to *Heuchera* 'Creole Nights', U.S. Plant patent application Ser. No. 13/385,801, the new cultivar has bicolor dark and light pink flowers rather than bicolor pink and white flowers.

This new *Heuchera* is uniquely distinguished by:

1. medium large, near black leaves with a slight white veil year round,
2. large, bicolor dark and light pink flowers that continue to bloom spring, summer and fall,
3. short, dark peduncles,
4. a well branched, medium large, mounding habit,
5. and excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a two-year-old plant of *Heuchera* 'Bella Notte' growing in a one gallon pot in a cold greenhouse in March in Canby, Oreg.

DETAILED PLANT DESCRIPTION

The following is a detailed description of the new *Heuchera* cultivar based on observations of two-year-old specimens growing in one gallon containers in a cold greenhouse in March in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart,* 5$^{th}$ edition.

Plant:

*Form.*—Basal rosette, herbaceous perennial.
*Hardiness.*—USDA Zone 4 to 9.
*Size.*—23 cm tall from top of the foliage to the ground and 41 cm wide.
*Habit.*—Mounding.
*Vigor.*—Excellent.

Leaf:

*Type.*—Simple.
*Arrangement.*—Rosette.
*Shape.*—Broadly ovate to orbicular.
*Lobing/division.*—5 to 7 shallow lobes.
*Venation.*—Palmate.

*Margins.*—Crenate.
*Apex.*—Mucronulate.
*Base.*—Cordate and overlapping.
*Blade size.*—Grows to 12 cm long and 14 cm wide.
*Texture.*—Leathery.
*Surface texture.*—Glandular on top and bottom.
*Petiole description.*—Grows to 16 cm long and 3 mm wide, glandular hairs, Greyed Purple 187B.
*Leaf color.*—Topside, spring, Greyed Purple N186A with veins Greyed Purple 184C; topside summer to winter Greyed Purple N186A with a slight veil Black 202D; bottom side color same for all seasons Greyed Purple 187A.

Inflorescence:
*Size.*—Grows to 6 cm wide and 15 cm long.
*Type.*—Thyrse.
*Number of flowers per thyrse.*—About 45.
*Number of thyrse.*—About 12 in the first spring flush, reblooming all summer.
*Peduncle.*—Grows to 22 cm long, 3 mm wide at base, Greyed Purple 187B, glandular hairs.
*Pedicel.*—Variable in size, with glandular hairs, Greyed Purple 187A.
*Bloom period.*—April through October in Canby, Oreg.

Flower bud:
*Size.*—4.5 mm wide and 7.5 mm long.
*Description.*—Glandular puberulent, ovoid, down facing.
*Color.*—Red Purple 62A on the bottom half to Red 52B on the top half.

Flower:
*Type.*—Perfect.
*Shape.*—Campanulate.
*Size.*—8 mm long and 6 mm wide.
*Corolla description.*—5 petals, 5 mm long and 2 mm wide, broadly spatulate, side margins mostly entire, tip acuminate and serrate to incised, glabrous on top and glandular on bottom side, White N155B on both sides.
*Calyx description.*—Campanulate, 8 mm long and 6 mm wide, with 5 lobes divided ½ way to the base, each 4 mm wide and 4 mm long, glandular hairs outside and glabrous inside, tips obtuse, margin entire; color both sides Red Purple N57C on top half and Red Purple 62C on bottom half.
*Stamen description.*—5 in number, filaments 2 mm long, White N155B, anthers 0.5 mm, Greyed Orange 170A, pollen none.
*Pistil description.*—1, 2-beaked, 5 mm long and 2 mm wide; Yellow Green 145C overall, ovary 2 mm long and 2 mm wide; style 3 mm long.
*Fragrance.*—None.
*Lastingness.*—Each thyrse blooms for about 3 weeks on the plant.

Fruit:
*Type.*—Two-beaked ovoid capsule.
*Fertility.*—Low.
*Color.*—Greyed Brown 199C.

Seed:
*Shape.*—Linear.
*Size.*—2 mm long.
*Color.*—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

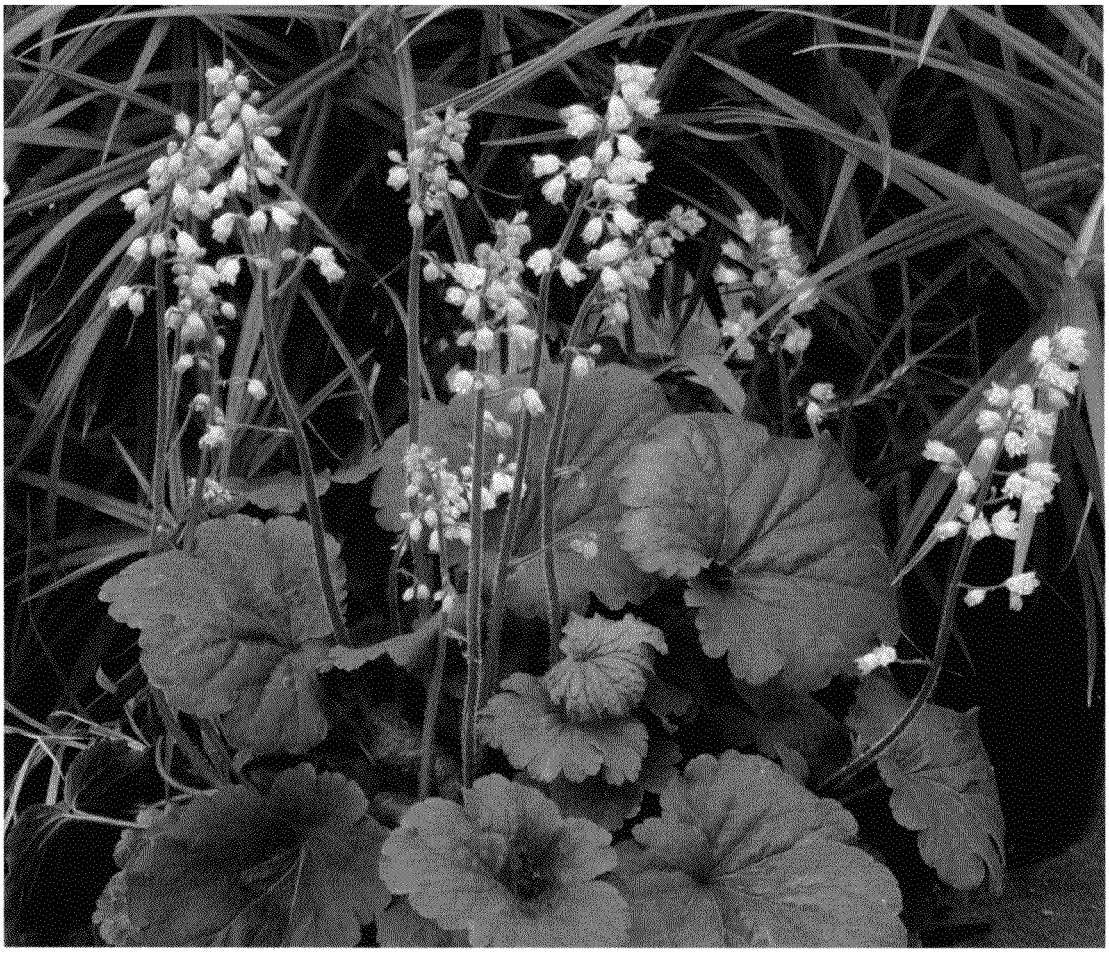

* * * * *